(12) United States Patent
Uchida et al.

(10) Patent No.: US 11,534,085 B2
(45) Date of Patent: Dec. 27, 2022

(54) SIGNAL PROCESSING DEVICE, RADAR SYSTEM, AND SIGNAL PROCESSING METHOD

(71) Applicant: SONY SEMICONDUCTOR SOLUTIONS CORPORATION, Kanagawa (JP)

(72) Inventors: Shigenori Uchida, Kanagawa (JP); Kenichi Kawasaki, Tokyo (JP); Hiroyuki Yamagishi, Tokyo (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 818 days.

(21) Appl. No.: 16/339,883

(22) PCT Filed: Oct. 11, 2017

(86) PCT No.: PCT/JP2017/036895
§ 371 (c)(1),
(2) Date: Apr. 5, 2019

(87) PCT Pub. No.: WO2018/079268
PCT Pub. Date: May 3, 2018

(65) Prior Publication Data
US 2019/0239773 A1    Aug. 8, 2019

(30) Foreign Application Priority Data

Oct. 31, 2016  (JP) .............................. JP2016-212461

(51) Int. Cl.
*A61B 5/113*    (2006.01)
*G01S 13/88*    (2006.01)
(Continued)

(52) U.S. Cl.
CPC ................ *A61B 5/113* (2013.01); *A61B 5/05* (2013.01); *G01S 13/32* (2013.01); *G01S 13/34* (2013.01);
(Continued)

(58) Field of Classification Search
CPC ......... A61B 5/024; A61B 5/05; A61B 5/0816; A61B 5/113; G01S 13/32; G01S 13/34; G01S 13/50; G01S 13/88
See application file for complete search history.

(56) References Cited

U.S. PATENT DOCUMENTS

2006/0284760 A1    12/2006  Natsume
2008/0074307 A1    3/2008   Boric-Lubecke
(Continued)

FOREIGN PATENT DOCUMENTS

CN    106659428 A    5/2017
CN    107272001 A    10/2017
(Continued)

OTHER PUBLICATIONS

International Search Report and Written Opinion of PCT Application No. PCT/JP2017/036895, dated Nov. 14, 2017, 09 pages of ISRWO.

*Primary Examiner* — Timothy X Pham
(74) *Attorney, Agent, or Firm* — Chip Law Group

(57) ABSTRACT

Provided is a signal processing device capable of distinguishing and measuring a plurality of measurement targets even with simple configuration. The signal processing device including a reception processing unit that receives a response to a predetermined signal transmitted from a transmission antenna, and a determination unit that determines the plurality of measurement targets by a response to a plurality of signals corresponding to a second direction
(Continued)

having a predetermined range different from a first direction having a predetermined range.

13 Claims, 13 Drawing Sheets

(51) Int. Cl.
*G01S 13/34* (2006.01)
*G01S 13/32* (2006.01)
*A61B 5/05* (2021.01)
*A61B 5/024* (2006.01)
*A61B 5/08* (2006.01)

(52) U.S. Cl.
CPC ............... *G01S 13/88* (2013.01); *A61B 5/024* (2013.01); *A61B 5/0816* (2013.01)

(56) References Cited

U.S. PATENT DOCUMENTS

| | | | |
|---|---|---|---|
| 2008/0077015 A1* | 3/2008 | Boric-Lubecke | G01S 13/888 600/453 |
| 2013/0135137 A1 | 5/2013 | Mulder et al. | |
| 2014/0058256 A1 | 2/2014 | De Jong | |
| 2017/0287334 A1* | 10/2017 | Slutsky | G01S 13/42 |
| 2017/0363738 A1* | 12/2017 | Kaino | G01S 13/584 |

FOREIGN PATENT DOCUMENTS

| | | |
|---|---|---|
| DE | 102006027678 A1 | 12/2006 |
| EP | 2417908 A1 | 2/2012 |
| JP | 2005331466 A | 12/2005 |
| JP | 2006-349456 A | 12/2006 |
| JP | 2013-538602 A | 10/2013 |
| JP | 2015-085065 A | 5/2015 |
| JP | 5861178 B1 | 2/2016 |
| JP | 2016-080398 A | 5/2016 |
| WO | 2012/020365 A1 | 2/2012 |

* cited by examiner

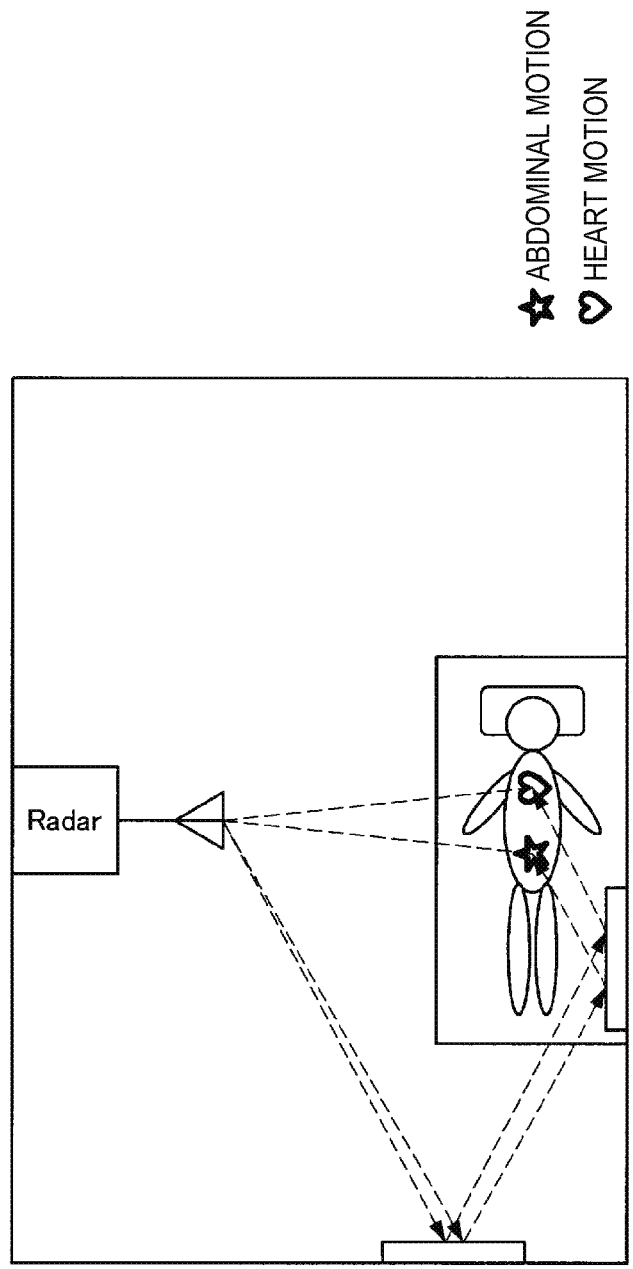

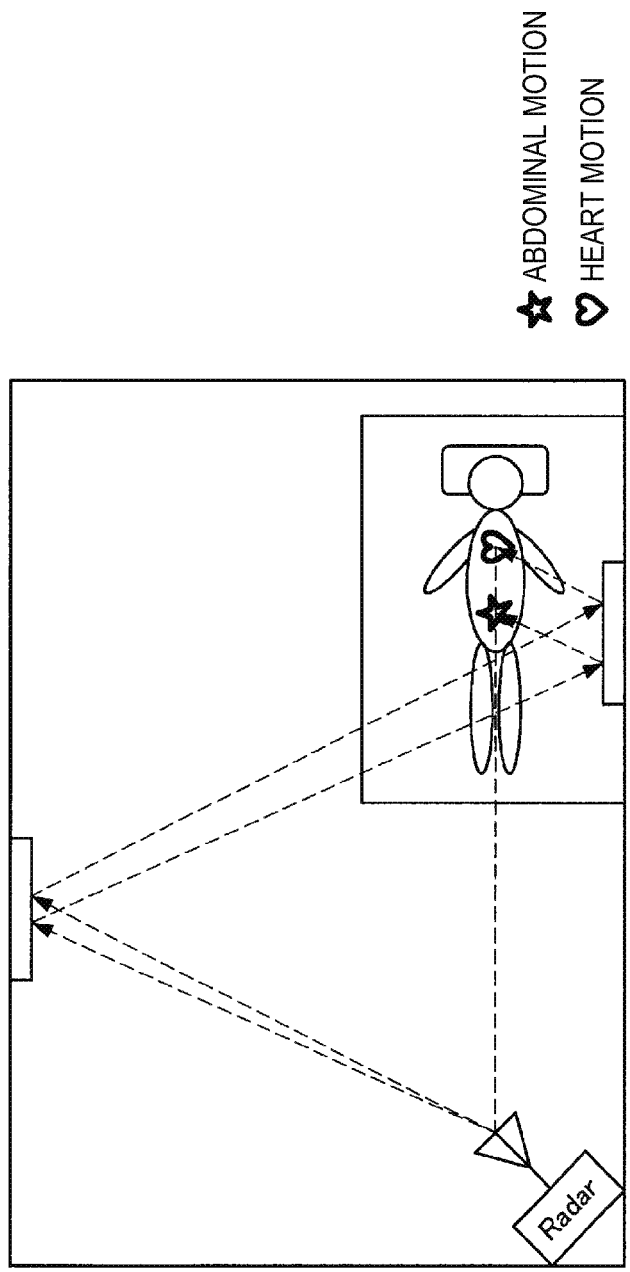

SIGNAL PROCESSING DEVICE, RADAR SYSTEM, AND SIGNAL PROCESSING METHOD

CROSS REFERENCE TO RELATED APPLICATIONS

This application is a U.S. National Phase of International Patent Application No. PCT/JP2017/036895 filed on Oct. 11, 2017, which claims priority benefit of Japanese Patent Application No. JP 2016-212461 filed in the Japan Patent Office on Oct. 31, 2016. Each of the above-referenced applications is hereby incorporated herein by reference in its entirety.

TECHNICAL FIELD

The present disclosure relates to a signal processing device, a radar system, and a signal processing method.

BACKGROUND ART

Techniques for measuring the state of an object using a radar system are developed, and in particular, a technique for measuring respiration, pulsation, or the like of a human body by using a radar system is disclosed (e.g., refer to Patent Literature 1).

CITATION LIST

Patent Literature

Patent Literature 1: JP 2016-156751A

DISCLOSURE OF INVENTION

Technical Problem

To distinguish between a plurality of measurement targets (e.g., chest and abdomen) in the radar system, it is necessary to distinguish between the plurality of measurement targets by the distance and angle from the radar system. The distinction between a plurality of measurement targets by rotating an antenna to perform scanning or providing a plurality of antennas to detect a phase causes to the complication of the radar system.

In view of this, the present disclosure provides a novel and improved signal processing device, radar system, and signal processing method, capable of distinguishing and measuring a plurality of measurement targets even with simple configuration.

Solution to Problem

According to the present disclosure, there is provided a signal processing device including: a reception processing unit configured to receive a response to a predetermined signal transmitted from a transmission antenna; and a determination unit configured to determine the plurality of measurement targets by a response to a plurality of signals corresponding to a second direction having a predetermined range different from a first direction having a predetermined range.

In addition, according to the present disclosure, there is provided a radar system including: a transmission antenna configured to output a predetermined signal; a reception antenna configured to receive a response to the predetermined signal transmitted from the transmission antenna; and a determination unit configured to determine the plurality of measurement targets by a response to a plurality of signals corresponding to a second direction having a predetermined range different from a first direction having a predetermined range.

In addition, according to the present disclosure, there is provided a signal processing method including: receiving a response to a predetermined signal transmitted from a transmission antenna; and determining the plurality of measurement targets by a response to a plurality of signals corresponding to a second direction having a predetermined range different from a first direction having a predetermined range.

Advantageous Effects of Invention

According to the present disclosure as described above, it is possible to provide a novel and improved signal processing device, radar system, and signal processing method, capable of distinguishing and measuring a plurality of measurement targets even with simple configuration.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 12 is a diagram illustrated to describe an example of how a radio wave is reflected twice and reaches a measurement target.

FIG. 13 is a diagram illustrated to describe an example of how a radio wave is reflected twice and reaches a measurement target.

MODE(S) FOR CARRYING OUT THE INVENTION

Figure 1:
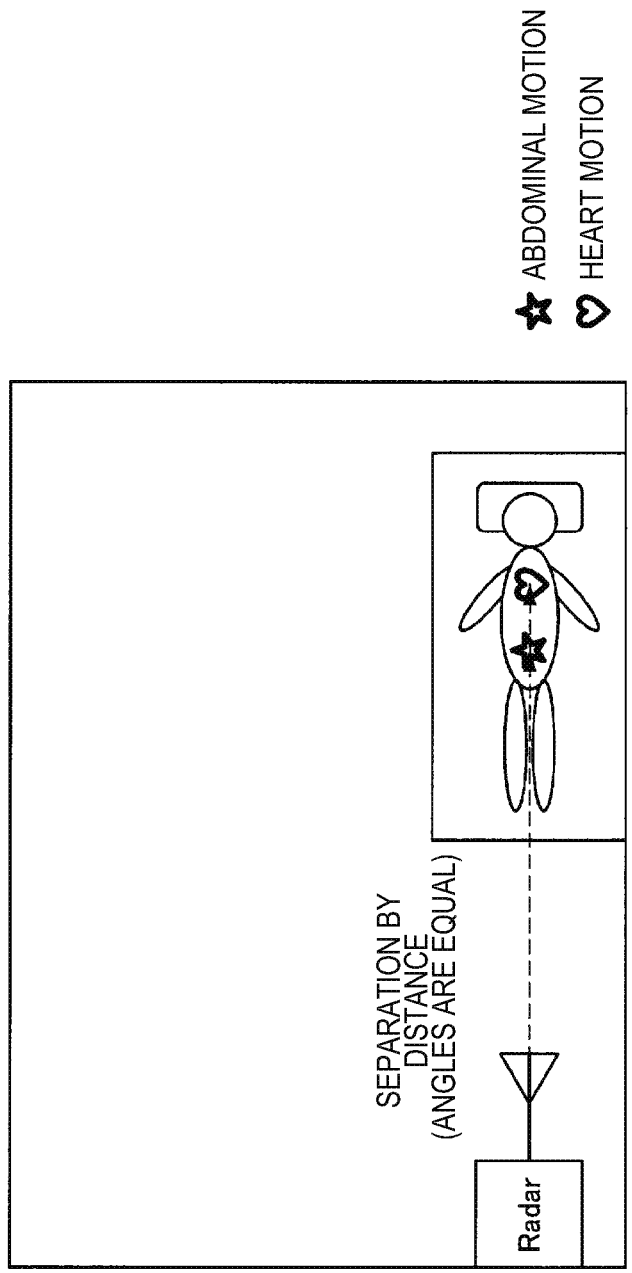
FIG. 1 is a diagram illustrated to describe how a plurality of measurement targets fails to be separated by a positional relationship between an installation position and the measurement target.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Moreover, the description will be given in the following order.
1. Embodiment of present disclosure
1.1. Overview
1.2. First configuration example and operation example
1.3. Second configuration example and operation example
2. Concluding remarks

1. Embodiment of Present Disclosure

1.1. Overview

An overview of an embodiment of the present disclosure is described, and then the embodiment of the present disclosure is described in detail.

As described above, techniques for measuring the state of an object using a radar system are developed, and in particular, a technique for measuring respiration, pulsation, or the like of a human body by using a radar system is disclosed. To distinguish between a plurality of measurement targets (e.g., chest and abdomen) in the radar system, it is necessary to distinguish between the plurality of measurement targets by the distance and angle from the radar system. In a case where the distinction between a plurality of measurement targets is achieved by rotating an antenna to perform scanning or providing a plurality of antennas to detect a phase, it is necessary to provide a mechanical mechanism for rotating the antenna or provide a plurality of antennas, which leads to complication of the radar system.

On the other hand, in a radar with simplified function that has distance resolution but does not have angular resolution like a single-antenna frequency-modulated continuous wave (FMCW) radar, a plurality of measurement targets (e.g., abdomen motion and heart motion) fails to be separated from each other by the positional relationship between the installation position and the measurement targets. FIG. 1 is a diagram illustrated to describe how the plurality of measurement targets (abdomen motion and heart motion) fails to be separated from each other by the positional relationship between the installation position and the measurement targets. In the example of FIG. 1, there is no angular resolution, so the distances from an antenna of the radar to the abdomen and the heart are substantially equal to each other. Thus, the abdomen motion and the heart motion fail to be separated from each other. Accordingly, such a radar having distance resolution but no angular resolution has restrictions on its installation position.

Figure 2:
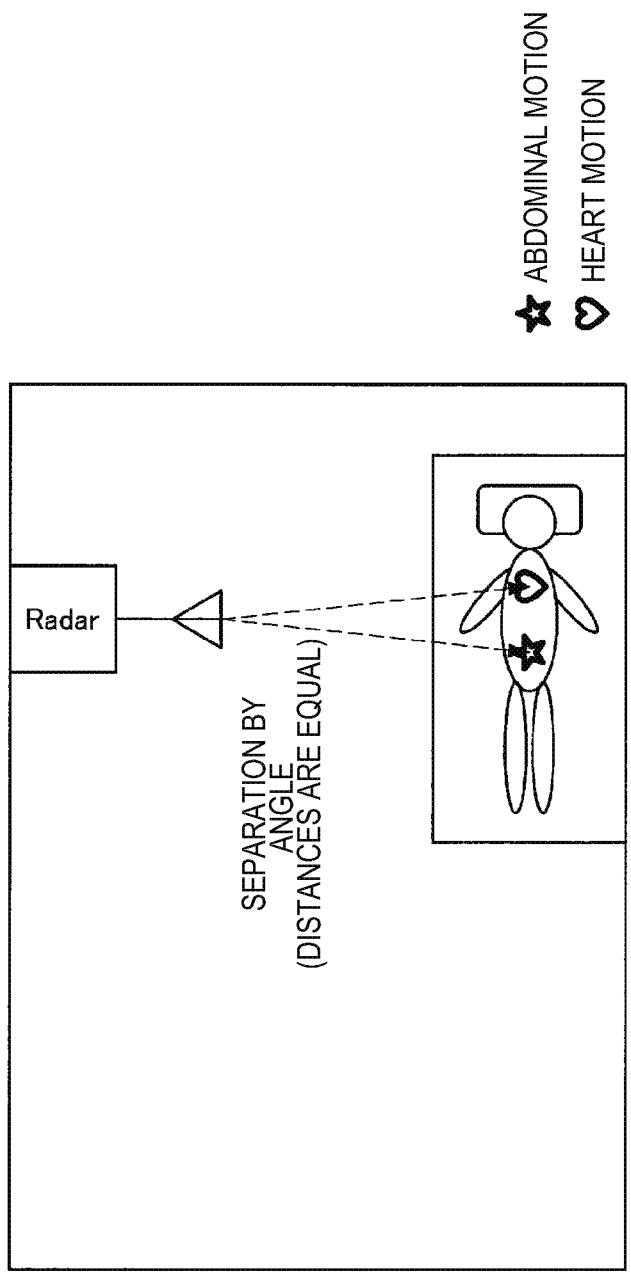
FIG. 2 is a diagram illustrated to describe how a plurality of measurement targets fails to be separated by a positional relationship between an installation position and the measurement target.

Further, in a radar that has angular resolution but does not have distance resolution, a plurality of measurement targets similarly fails to be separated from each other by the positional relationship between the installation position and the measurement targets. FIG. 2 is a diagram illustrated to describe how a plurality of measurement targets (abdomen motion and heart motion) fails to be separated from each other by the positional relationship between the installation position and the measurement targets. In the example of FIG. 2, there is no distance resolution, so the directions from an antenna of the radar toward the abdomen and the heart are substantially equal to each other. Thus, the abdomen motion and heart motion fail to be separated from each other. Accordingly, such a radar having angular resolution but no distance resolution has also restrictions on its installation position.

In view of this, in consideration of the above-mentioned points, those who conceived the present disclosure have conducted intensive studies on the technology capable of separating a plurality of measurement targets independently of the positional relationship between the installation position and the measurement targets even in a radar with simple configuration, for example, a radar having distance resolution but no angular resolution or a radar having angular resolution but no distance resolution. Accordingly, those who conceived the present disclosure have devised the technology capable of separating a plurality of measurement targets independently of the positional relationship between the installation position and the measurement targets even in a radar with simple configuration, for example, a radar having distance resolution but no angular resolution or a radar having angular resolution but no distance resolution.

The overview of the embodiment of the present disclosure is described above. Then, the embodiment of the present disclosure is described in detail.

1.2. First Configuration Example and Operation Example

A first configuration example of the embodiment of the present disclosure is now described. The first configuration example focuses on a radar having distance resolution but no angular resolution.

Figure 3:
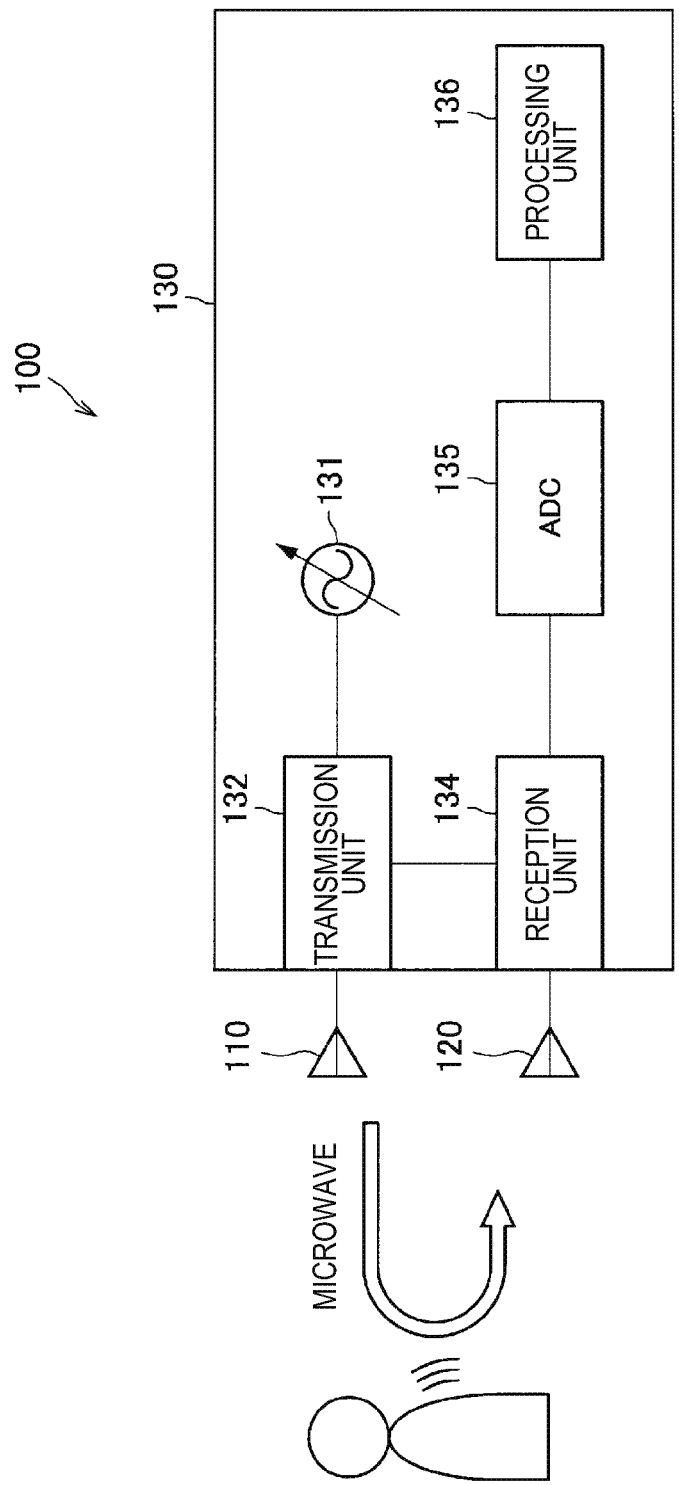
FIG. 3 is a diagram illustrated to describe a configuration example of a radar system 100 according to an embodiment of the present disclosure.

FIG. 3 is a diagram illustrated to describe a configuration example of a radar system 100 according to the embodiment of the present disclosure. The configuration example of the radar system 100 according to the embodiment of the present disclosure is now described with reference to FIG. 3.

As illustrated in FIG. 3, the radar system 100 according to the embodiment of the present disclosure includes a transmission antenna 110, a reception antenna 120, and a signal processing device 130.

The radar system 100 illustrated in FIG. 3 is a radar system having distance resolution but no angular resolution, and is, in one example, a single-antenna FMCW radar.

The transmission antenna 110 emits a predetermined signal generated by the signal processing device 130 as a radio wave into a space. The reception antenna 120 receives a radio wave (sensor data), which is emitted from the transmission antenna 110 and reflected by an object, and converts it into a signal. The reception antenna 120 sends the signal converted from the radio wave to the signal processing device 130.

The signal processing device 130 executes processing regarding signal transmission and reception to and from the radar system 100. The signal processing device 130 includes an oscillator 131, a transmission unit 132, a reception unit 134, an AD converter 135, and a processing unit 136.

The oscillator 131 is a signal source whose frequency varies with time. The transmission unit 132 executes processing on the signal emitted from the transmission antenna 110. In one example, if the radar system 100 is an FMCW radar, predetermined frequency modulation is performed on a continuous wave oscillated at a predetermined frequency by the oscillator 131.

The reception unit 134 executes processing on the signal (sensor data) received by the reception antenna 120. In one example, the reception unit 134 performs processing of mixing the signal sent from the reception antenna 120 and the modulated signal emitted from the transmission antenna 110 and demodulating the mixed signal. In addition, the reception unit 134 executes processing of acquiring a temporal change in displacements (responses) with respect to the demodulated signal. The reception unit 134 sends a result obtained by executing the processing on the signal received by the reception antenna 120 to the AD converter 135.

The AD converter 135 converts the result of the processing in the reception unit 134 into a digital signal. The AD converter 135 sends the signal converted into the digital signal to the processing unit 136.

The processing unit 136 executes signal processing on the digital signal converted by the AD converter 135. In the present embodiment, the processing unit 136 executes processing of calculating a response for each distance from the radar system 100 and detecting the state of measurement target in the space where the radar system 100 is installed, on the basis of the digital signal converted by the AD converter 135. Although the number of measurement targets may be one, it is assumed that there is a plurality of measurement targets in the present embodiment. In one example, if the measurement target in the space is a human, the processing unit 136 detects a heartbeat or respiration of the human. More specifically, the processing unit 136 executes processing of detecting the state of a plurality of measurement targets in the space by using a response close in time from a transmission time point of the radio wave from the transmission antenna 110.

Here, as described above, in the case of a radar having distance resolution but no angular resolution, objects equidistant from the radar fail to be separated. Thus, in a case where a distance from the radar system 100 having distance resolution but no angular resolution to the chest of a human is substantially equal to a distance to the abdomen, it is necessary to detect states of the chest and the abdomen.

In view of this, in a case where a plurality of measurement targets is not found by a response close in time from the transmission time point of the radio wave, the processing unit 136 executes processing of detecting the state of a plurality of measurement targets in the space by using another response different in time from it. In other words, the processing unit 136 executes processing of detecting the state of a plurality of measurement targets in the space by using a response to the radio wave reaching the measurement target through reflection at least once from the transmission antenna 110, rather than the radio wave directly reaching the measurement target from the transmission antenna 110.

Figure 4:
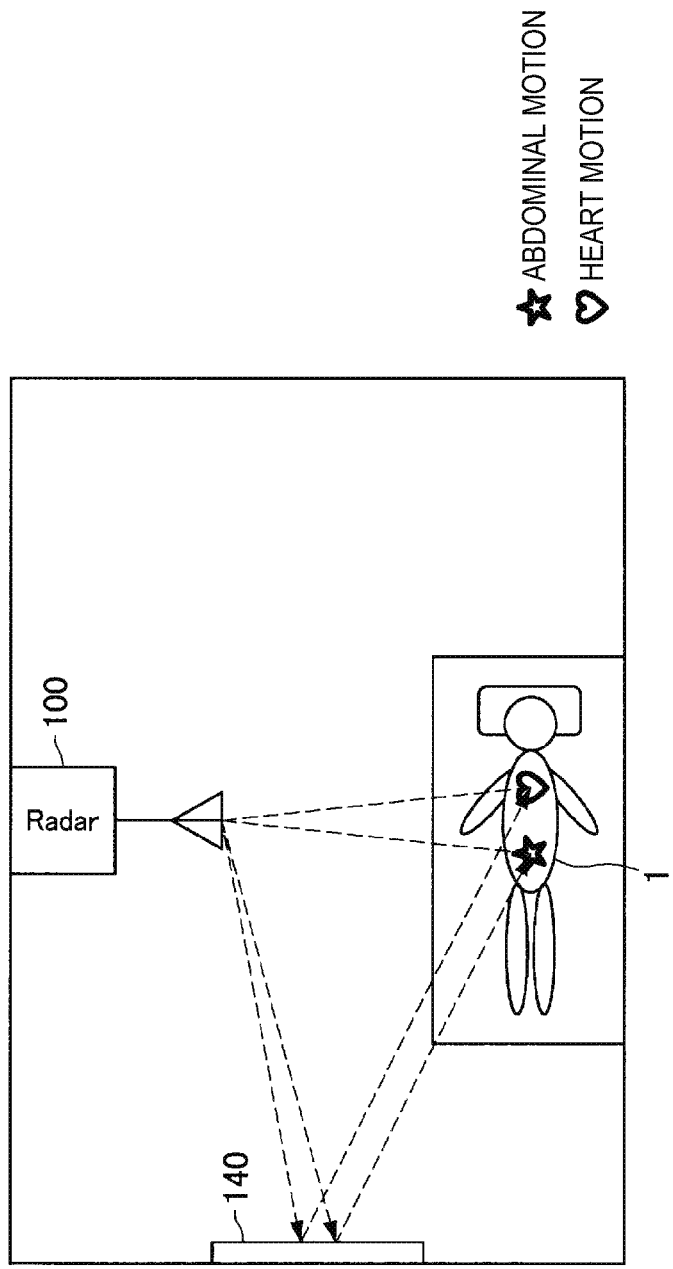
FIG. 4 is a diagram illustrated to describe how a radio wave from the radar system 100 directly reaches a human 1 as a measurement target and how the radio wave is reflected by a reflecting plate 140 on the wall surface and reaches it.

FIG. 4 is a diagram illustrated to describe how a radio wave from the radar system 100 directly reaches a human 1 as a measurement target and how the radio wave is reflected by a reflecting plate 140 on the wall surface and reaches it. FIG. 4 illustrates how the radar system 100 detects abdomen motion and heart motion of the human 1. The radar system 100 does not have angular resolution, so it fails to distinguish the direction of the emitted radio wave. However, the radar system 100 has distance resolution, so it is possible to distinguish the difference in distance. Thus, if there is a difference in distances between the measurement targets, the radar system 100 is capable of detecting the abdomen motion and the heart motion of the human 1 while distinguishing them from each other. Thus, the radar system 100 finds the responses to the radio waves, which are reflected by the reflecting plate 140 on the wall surface and reach the abdomen and the chest of the human 1 as illustrated in FIG. 4, thereby detecting the abdomen motion and the heart motion of the human 1 while distinguishing them from each other.

Moreover, the reflecting plate 140 is used to suppress scattering of the radio wave emitted from the radar system 100, and, as its material, a conductor, a dielectric, a metamaterial, a magnetic material, and the like are conceived to be used. The shape of the reflecting plate 140 may be a flat plate or a sphere. Moreover, if there is no fear of scattering of the radio wave emitted by the radar system 100 even without the reflecting plate 140, the reflecting plate 140 is not necessarily provided.

Figure 5:
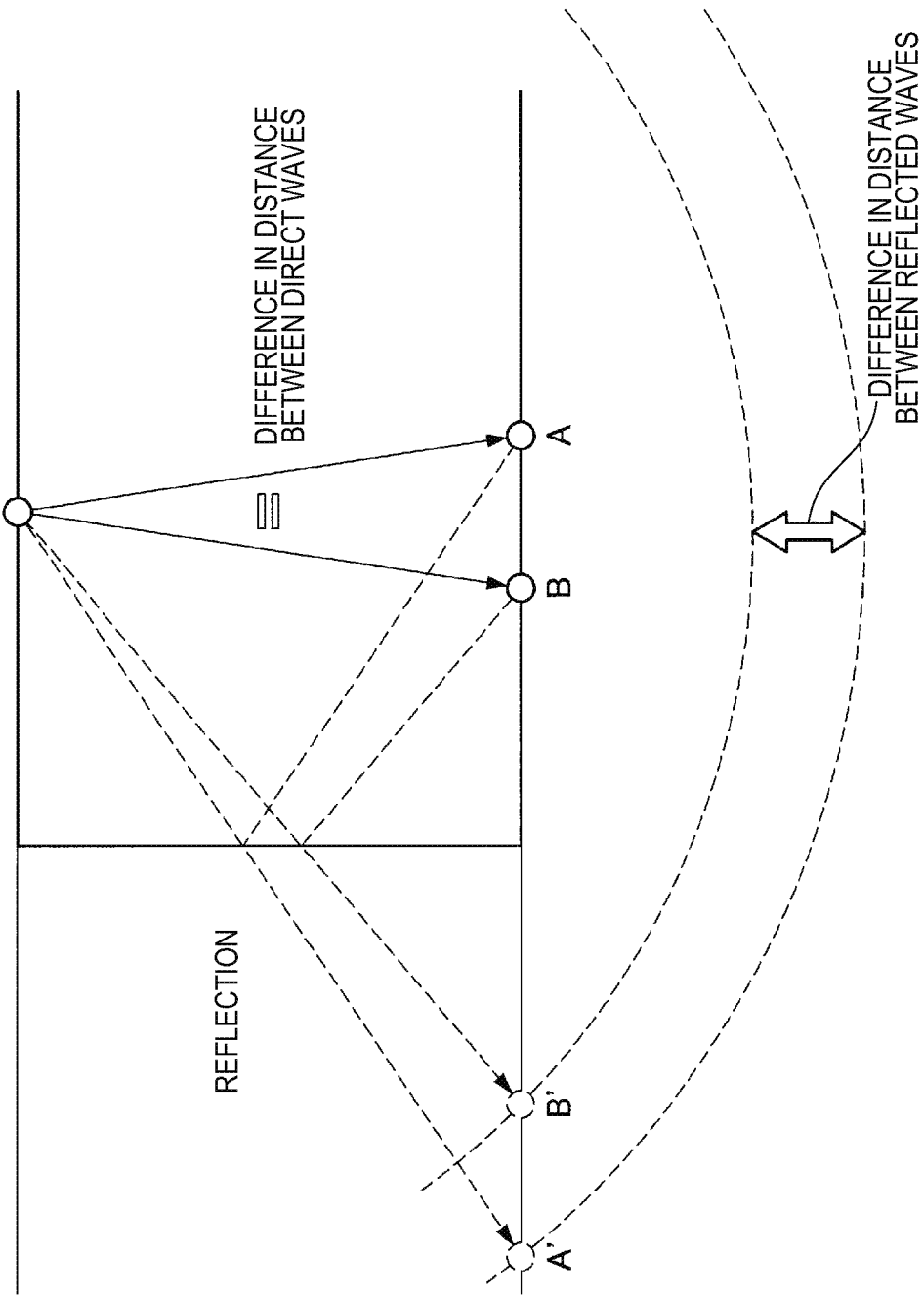
FIG. 5 is a diagram illustrated to describe a difference in distance from the radar system 100 to measurement targets.

FIG. 5 is a diagram illustrated to describe a difference in distances from the radar system 100 to measurement targets between a case where the radio waves from the radar system 100 directly reach the measurement targets (case where direct waves reach) and a case where the radio waves are reflected once and then reach the measurement targets (case where reflected waves reach).

In the example illustrated in FIG. 5, in the case where the radio waves from the radar system 100 directly reach measurement targets (point A and point B), a distance from the radar system 100 to the point A is equal to a distance to the point B. However, in the case where the radio waves from the radar system 100 are reflected once and reach the points A and B, the distance from the radar system 100 to the point A different from the distance to the point B. Thus, the two measurement targets fail to be distinguished from each other by the responses to the direct waves, but it is possible to distinguish the two measurement targets by finding the responses to the reflected waves.

Figure 6:
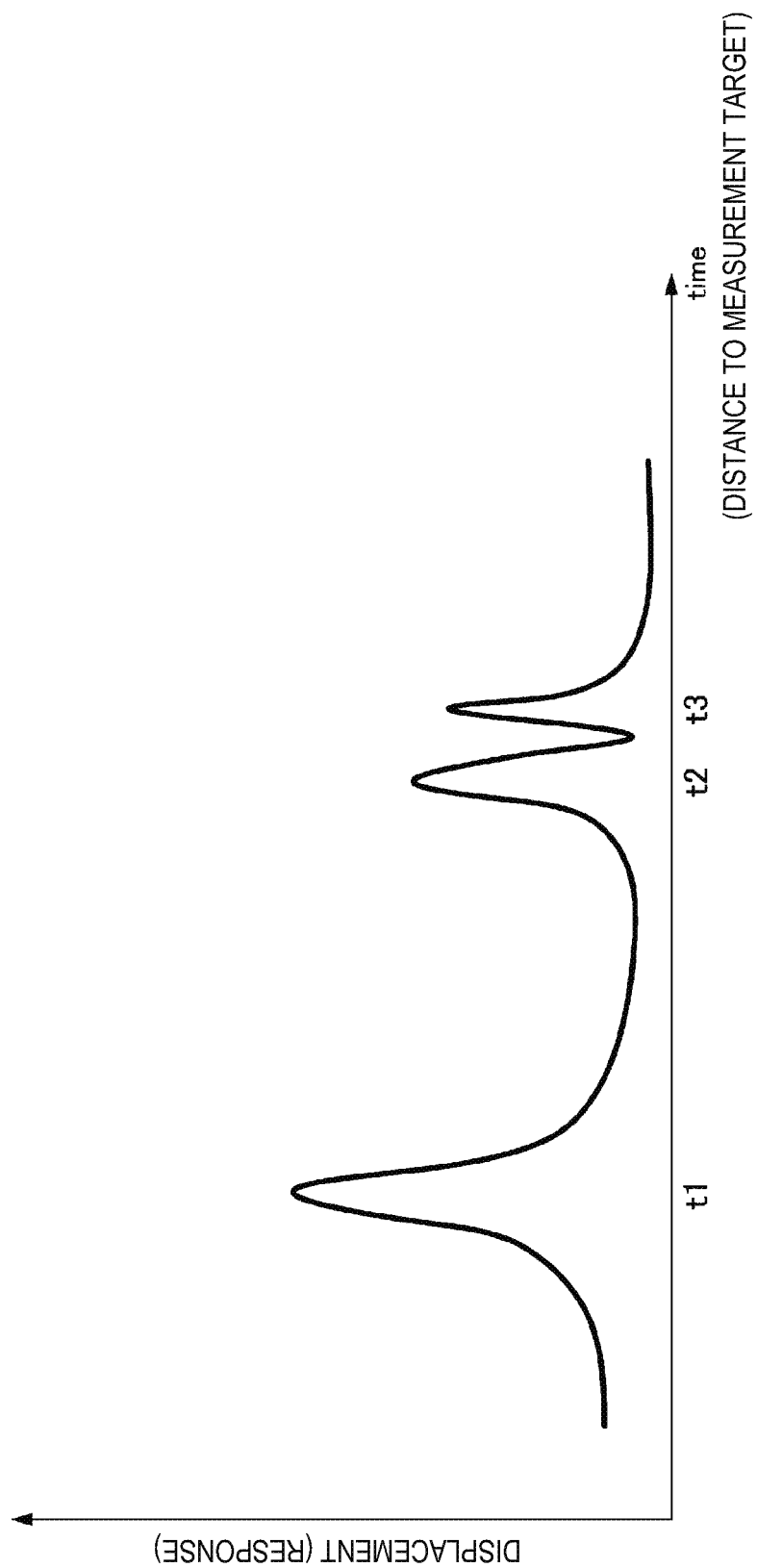
FIG. 6 is a diagram illustrated to describe an example of a response of sensor data received by the radar system 100.

FIG. 6 is a diagram illustrated to describe an example of a response of sensor data received by the radar system 100 arranged as illustrated in FIG. 4. FIG. 6 illustrates a graph where the horizontal axis represents the elapsed time after transmission of radio waves from the radar system 100, that is, the distance from the radar system 100 to the measurement targets, and the vertical axis represents the displacement (response) of the measurement targets.

In the graph illustrated in FIG. 6, it is assumed that a response in which a peak appears at time t1 is a response to a direct wave, and responses in which peaks appear at times t2 and t3 are responses to a reflected wave.

As illustrated in FIG. 6, the response that has a peak appearing at time t1 and has a predetermined time range before and after including time t1 (a range of a predetermined time before and after including a certain time is also referred to as "time group") is a response to each of the points A and B. In other words, two measurement targets fail to be distinguished by the response in which a peak appears at time t1.

On the other hand, as illustrated to FIG. 6, the responses that have peaks appearing at times t2 and t3 and have the time group including times t2 and t3 are responses to the respective points A and B. In other words, it is possible to distinguish two measurement targets by the responses in which peaks appear at times t2 and t3.

Thus, the processing unit 136 is capable of distinguishing a plurality of measurement targets by calculating a response for each distance and, in the case where the plurality of measurement targets fail to be distinguished by the response having shorter elapsed time after transmitting the radio wave (i.e., the response in which a peak appears at time t1 in FIG. 6), by finding the response having longer elapsed time (i.e., the responses in which peaks appear at times t2 and t3 in FIG. 6).

Figure 7:
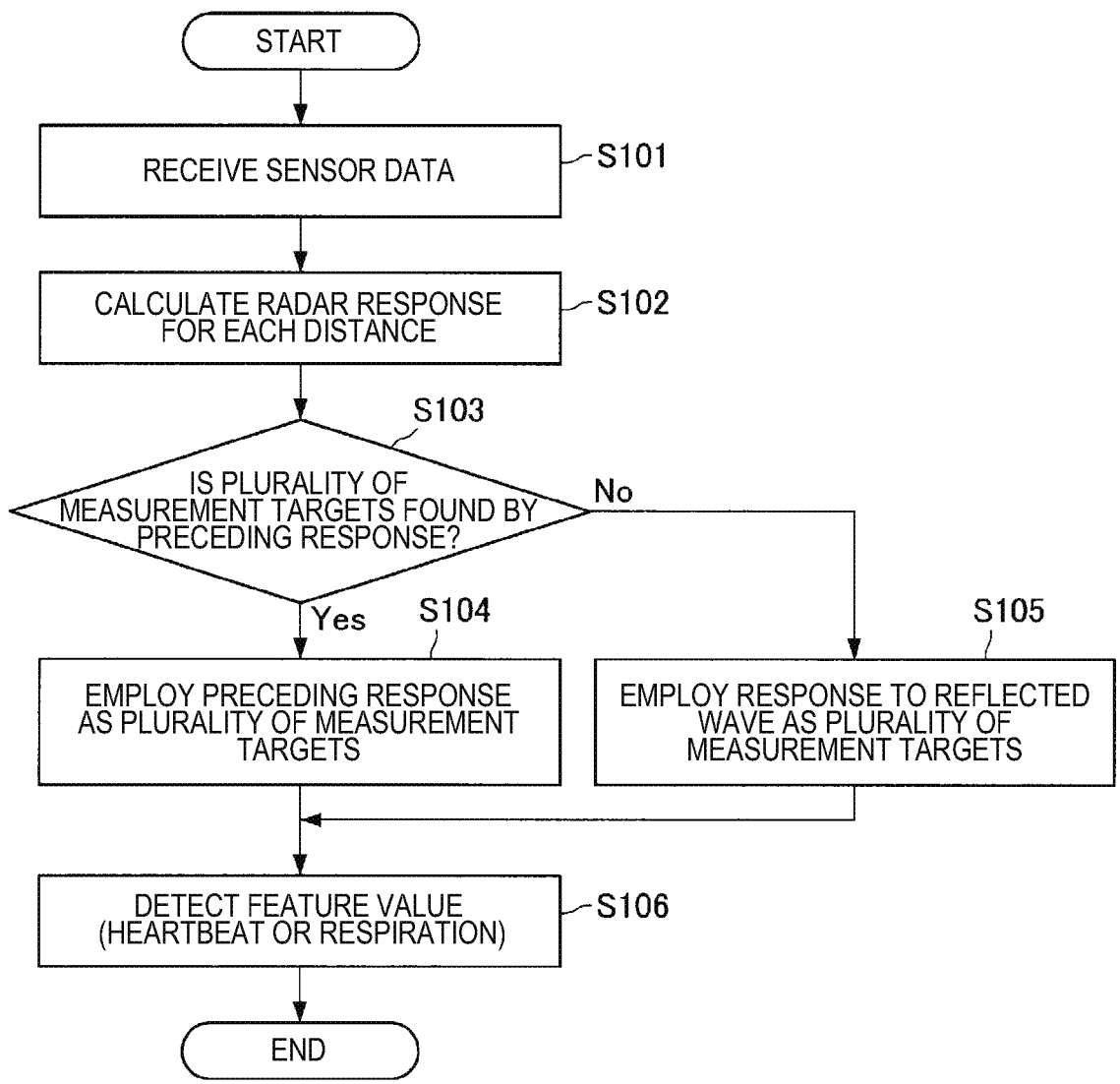
FIG. 7 is a flowchart illustrating an operation example of the radar system 100 according to the present embodiment.

FIG. 7 is a flowchart illustrating an operation example of the radar system 100 according to the embodiment of the present disclosure. FIG. 7 illustrates an operation example of the radar system 100 in distinguishing and detecting a plurality of measurement targets. The operation example of the radar system 100 according to the embodiment of the present disclosure is now described with reference to FIG. 7.

The radar system 100, when receiving sensor data on the measurement target for the radio wave emitted from the transmission antenna 110 through the reception antenna 120 (step S101), calculates a radar response for each distance from the sensor data (step S102). The calculation of the radar response in step S102 is executed by, in one example, the reception unit 134.

The radar system 100, when calculating the radar response for each distance, then determines whether or not a plurality of measurement targets can be found by the preceding response that is a response in which a peak appears in a shorter elapsed time after transmitting the radio wave (step S103). The determination processing in step S103 is executed by, in one example, the processing unit 136. Although the range that serves as a reference for determination of whether or not a plurality of measurement targets can be found varies depending on the measurement targets, if the measurement target is, in one example, the abdomen and the chest of a human, the determination of whether or not a plurality of measurement targets is found is performed in the distance range from approximately several tens of centimeters to one meter.

In a case where a plurality of measurement targets is found by the preceding response as a result of the determination processing in step S103 (Yes in step S103), the radar system 100 employs the preceding response as a plurality of measurement targets (step S104). On the other hand, in a case where a plurality of measurement targets is not found by the preceding response as a result of the determination processing in step S103 (No in step S103), the radar system 100 employs a plurality of responses in which peaks appear at a point in time which is later in time (farther in distant) as a plurality of measurement targets (step S105). The plurality of responses employed in this step S105 may be a plurality of responses in which peaks appear in the distance range from approximately several tens of centimeters to one meter if the measurement target is, in one example, the abdomen and chest of a human. The processing of step S104 or step S105 is executed by, in one example, the processing unit 136.

Then, the radar system 100 detects the state of measurement targets, for example, respiration, heartbeat, or the like using the response employed in step S104 or step S105 (step S106). The processing of step S106 is executed by, in one example, the processing unit 136.

The radar system 100 according to the embodiment of the present disclosure is capable of detecting the state of a plurality of measurement targets by executing the series of operations described above even if it has distance resolution but does not have angular resolution.

1.3. Second Configuration Example and Operation Example

A second configuration example of the embodiment of the present disclosure is now described. The second configuration example focuses on a radar having angular resolution but no distance resolution.

Figure 8:
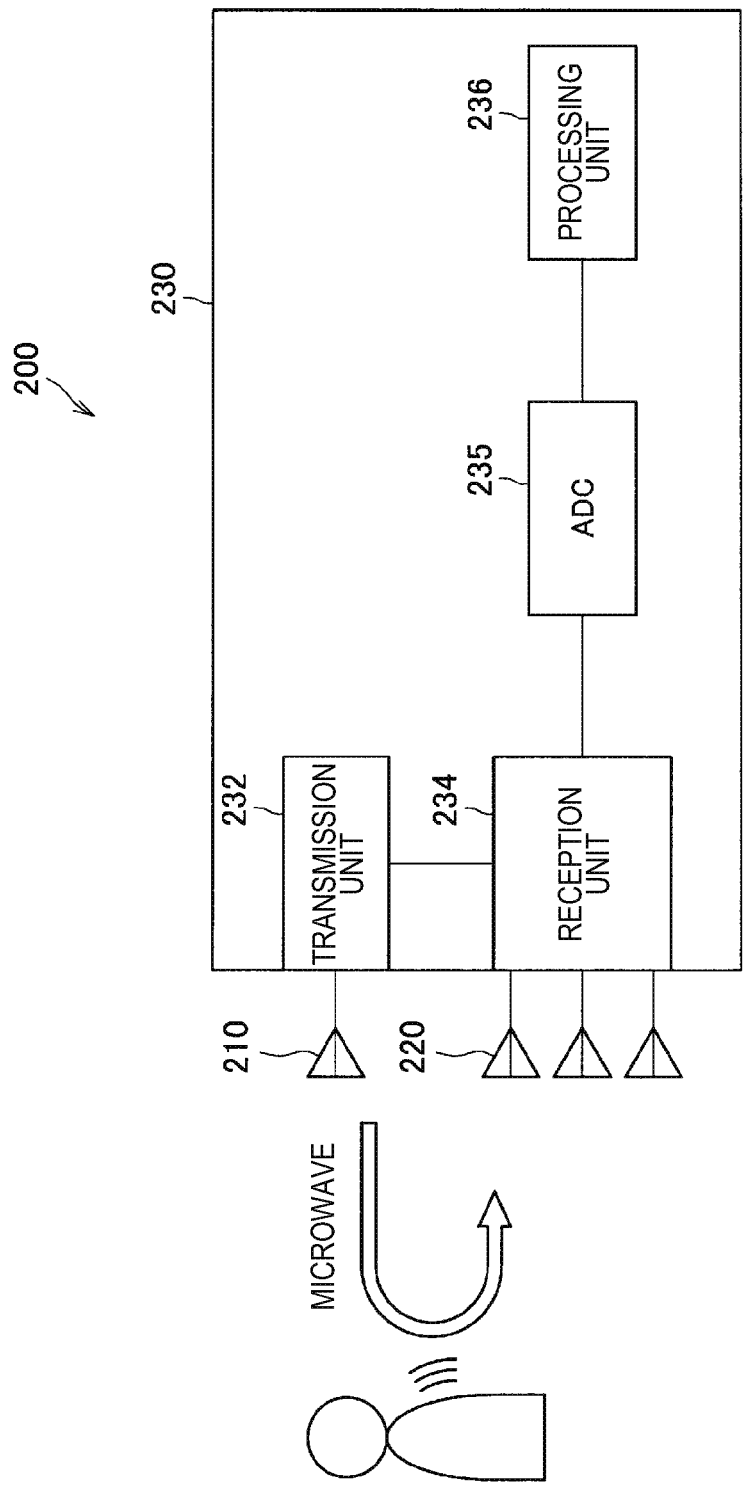
FIG. 8 is a diagram illustrated to describe a configuration example of a radar system 200 according to the present embodiment.

FIG. 8 is a diagram illustrated to describe a configuration example of a radar system 200 according to the embodiment of the present disclosure. The configuration example of the radar system 200 according to the embodiment of the present disclosure is now described with reference to FIG. 8.

As illustrated in FIG. 8, the radar system 200 according to the embodiment of the present disclosure includes a transmission antenna 210, a reception antenna 220, and a signal processing device 230.

The radar system 200 illustrated in FIG. 8 is a radar device having angular resolution but no distance resolution, and is, in one example, a multi-antenna CW radar.

The transmission antenna 210 emits a predetermined signal generated by the signal processing device 230 as a radio wave into a space. The reception antenna 220, which includes a plurality of antenna elements, receives a radio wave (sensor data), which is emitted from the transmission antenna 210 and reflected by an object, and converts it into a signal. The reception antenna 220 sends the signal converted from the radio wave to the signal processing device 230.

The signal processing device 230 executes processing regarding signal transmission and reception to and from the radar system 200. The signal processing device 230 includes a transmission unit 232, a reception unit 234, an AD converter 235, and a processing unit 236.

The transmission unit 232 executes processing on a signal emitted from the transmission antenna 210. In one example, if the radar system 100 is the CW radar, the processing of emitting a continuous wave at a predetermined frequency as a radio wave from the transmission antenna 210 is executed.

The reception unit 234 executes processing on a signal (sensor data) received by the reception antenna 220. In one example, the reception unit 234 performs processing of mixing a signal sent from the reception antenna 220 and a signal emitted from the transmission antenna 210 (processing of generating a beat signal including a frequency component of a difference between a received signal and a transmitted signal). In addition, the reception unit 234 executes processing of acquiring a temporal change in displacements (responses) with respect to the signal. The reception unit 234 sends the result of processing on the signal received by the reception antenna 120 to the AD converter 235.

The AD converter 235 converts the result of the processing in the reception unit 234 into a digital signal. The AD converter 235 sends the signal converted into the digital signal to the processing unit 236.

The processing unit 236 executes signal processing on the digital signal converted by the AD converter 235. In the present embodiment, the processing unit 236 executes processing of calculating a response for each distance from the radar system 200 and detecting the state of measurement target in the space where the radar system 200 is installed, on the basis of the digital signal converted by the AD converter 235. Although the number of measurement targets may be one, it is assumed that there is a plurality of measurement targets in the present embodiment. In one example, if the measurement target in the space is a human, the processing unit 236 detects a heartbeat or respiration of the human. More specifically, the processing unit 236 executes processing of detecting the state of a plurality of measurement targets in the space by using a response close in time from a transmission time point of the radio wave from the transmission antenna 210.

Here, as described above, in the case of a radar having angular resolution but no distance resolution, objects equiangular from the radar fail to be separated. Thus, in a case where an angle from the radar system 200 having angular resolution but no distance resolution to the chest of a human is substantially equal to an angle to the abdomen, it is necessary to detect states of the chest and the abdomen.

In view of this, in a case where a plurality of measurement targets is not found by a response in the prescribed transmission direction of the radio wave, the processing unit 236 executes processing of detecting the state of a plurality of measurement targets in the space by using another response different in angle from it. In other words, the processing unit 236 executes processing of detecting the state of a plurality of measurement targets in the space by using a response to the radio wave reaching the measurement target through reflection at least once from the transmission antenna 210, rather than the radio wave directly reaching the measurement target from the transmission antenna 210.

Figure 9:
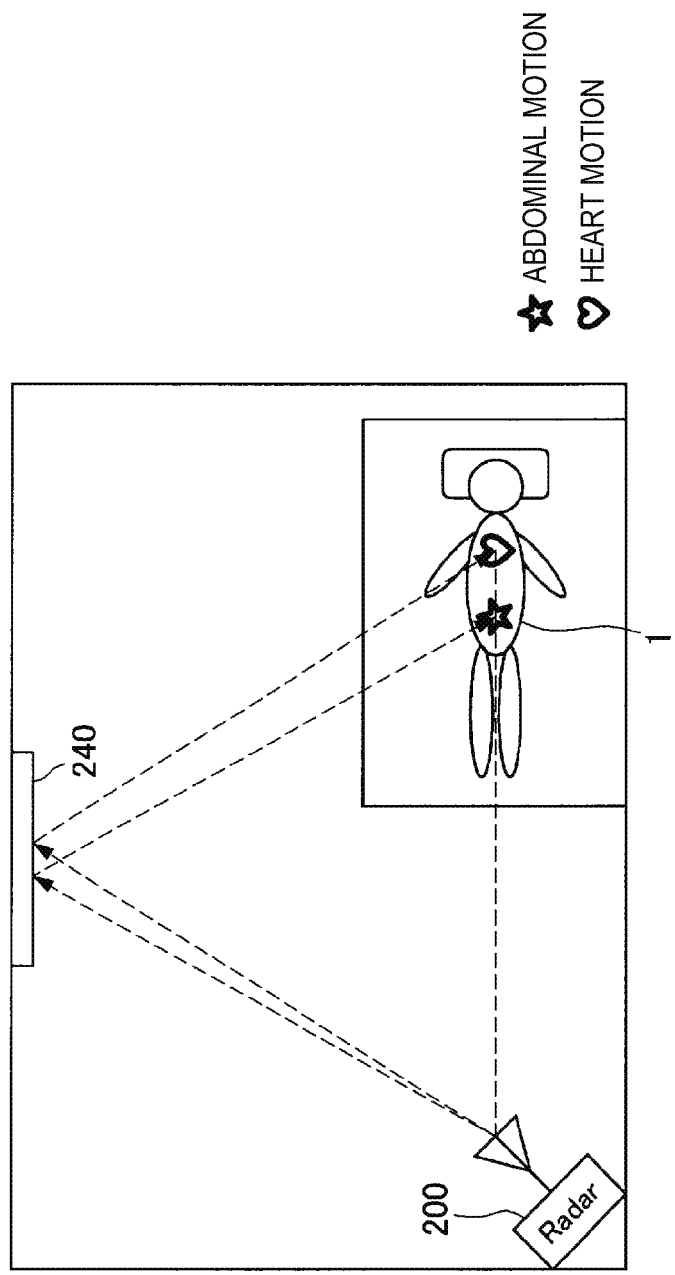
FIG. 9 is a diagram illustrated to describe how a radio wave from the radar system 200 directly reaches the human 1 as a measurement target and how the radio wave is reflected by a reflecting plate 240 on the wall surface and reaches it.

FIG. 9 is a diagram illustrated to describe how a radio wave from the radar system 200 directly reaches the human 1 as a measurement target and how the radio wave is reflected by a reflecting plate 240 on the wall surface and reaches it. FIG. 9 illustrates how the radar system 200 detects the abdomen motion and the heart motion of the human 1.

The radar system 200 does not have distance resolution, so the differences in distances to the measurement targets fail to be distinguished. However, the radar system 200 has angular resolution, so it capable of distinguishing the difference in angles. Thus, if there is a difference in angles between the measurement targets, the radar system 200 is capable of detecting the abdomen motion and the heart motion of the human 1 while distinguishing them from each other. Thus, the radar system 100 finds the responses to the radio waves, which are reflected by the reflecting plate 240 on the wall surface and reach the abdomen and the chest of the human 1 as illustrated in FIG. 9, thereby detecting the abdomen motion and the heart motion of the human 1 while distinguishing them from each other.

Moreover, the reflecting plate 240 is used to suppress scattering of the radio wave emitted from the radar system 200, and, as its material, a conductor, a dielectric, a metamaterial, a magnetic material, and the like are conceived to be used. The shape of the reflecting plate 240 may be a flat plate or a sphere. Moreover, if there is no fear of scattering of the radio wave emitted by the radar system 200 even without the reflecting plate 240, the reflecting plate 240 is not necessarily provided.

Figure 10:
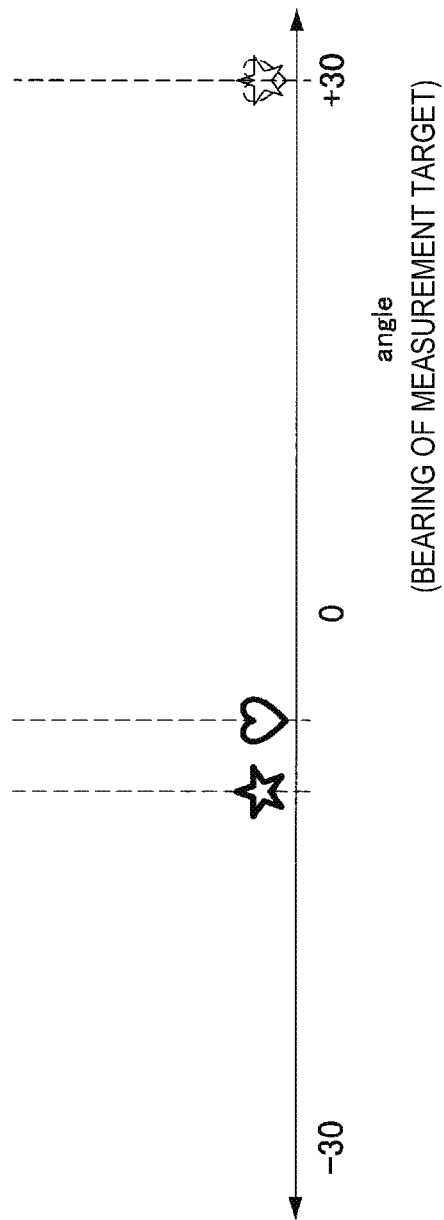
FIG. 10 is a diagram illustrated to describe an example of a response of sensor data received by the radar system 200.

FIG. 10 is a diagram illustrated to describe an example of a response of sensor data received by the radar system 200 arranged as illustrated in FIG. 9. FIG. 9 illustrates a graph where the horizontal axis represents the angle of the direction in which the radar system 200 transmits the radio wave and the vertical axis represents the response to the measurement targets.

In FIG. 10, in a range of a predetermined angle including a bearing of +30 degrees (a range of predetermined angles including an angle is also referred to as "angle group"), the abdomen and chest of the human 1 as viewed from the radar system 200 are in the same bearing, so the abdomen motion and heart motion of the human 1 fail to be distinguished. On the other hand, FIG. 10 illustrates that, in the angle group including the bearing of approximately minus 5 to 10 degrees, the passage through the reflecting plate 240 from the radar system 200 allows the abdomen motion and heart motion of the human 1 to be distinguished because the abdomen and the chest of the human 1 are in different bearings.

Thus, in a case where the processing unit 236 calculates the response in the prescribed direction but it fails to distinguish a plurality of measurement targets by the response in the prescribed direction, the processing unit 236 is capable of distinguishing the plurality of measurement targets from each other by finding a response to a radio wave emitted toward a different direction.

Figure 11:
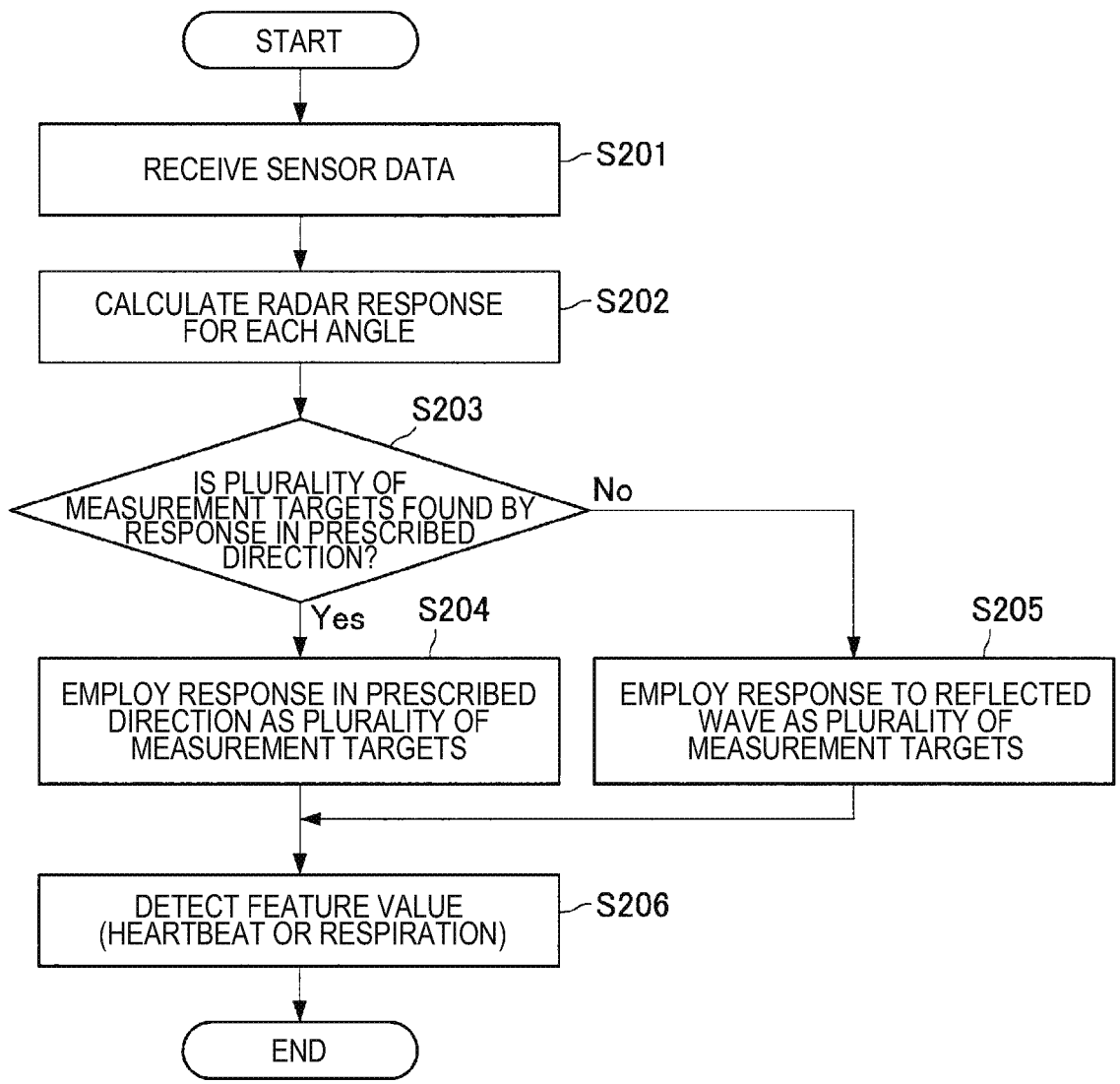
FIG. 11 is a flowchart illustrating an operation example of the radar system 200 according to the present embodiment.

FIG. 11 is a flowchart illustrating an operation example of the radar system 200 according to the embodiment of the present disclosure. FIG. 11 illustrates an operation example of the radar system 200 in distinguishing and detecting a plurality of measurement targets. The operation example of the radar system 200 according to the embodiment of the present disclosure is now described with reference to FIG. 11.

The radar system 200, when receiving sensor data on the measurement target for the radio wave emitted from the transmission antenna 210 through the reception antenna 220 (step S201), calculates a radar response for each angle from the sensor data (step S202). The calculation of the radar response in step S202 is executed by, in one example, the reception unit 234.

When the radar response for each angle is calculated, then the radar system 200 determines whether or not a plurality of measurement targets is found by the response in the prescribed direction (step S203). The determination processing in step S203 is executed by, in one example, the processing unit 236. Although the range that serves as a reference for determination of whether or not a plurality of measurement targets is found varies depending on the measurement targets, if the measurement target is, in one example, the abdomen and chest of a human, the determination of whether or not a plurality of measurement targets is found is performed in the range of approximately 5 degrees in angle.

In a case where a plurality of measurement targets is found by the response in the prescribed direction as a result of the determination processing in step S203 (Yes in step S203), the radar system 200 employs a response in that direction as a plurality of measurement targets (step S204). On the other hand, in a case where a plurality of measurement targets is not found by the response in the prescribed direction as a result of the determination processing in step S203 (No in step S203), the radar system 200 employs a plurality of responses in a direction different from the prescribed direction as a plurality of measurement targets (step S205). The plurality of responses employed in this step S205 may be a plurality of responses generated in an angular range of approximately 5 to 10 degrees in the case where the measurement target is, in one example, the abdomen and chest of a human. The processing of step S204 or step S205 is executed by, in one example, the processing unit 236.

Then, the radar system 200 detects the state of measurement targets, for example, respiration, heartbeat, or the like using the response employed in step S204 or step S205 (step S206). The processing of step S206 is executed by, in one example, the processing unit 236.

The radar system 200 according to the embodiment of the present disclosure is capable of detecting the state of a plurality of measurement targets by executing the series of operations described above even if it has angular resolution but does not have distance resolution.

In both of the first configuration example and the second configuration example, in the case where a plurality of measurement targets fails to be distinguished by a direct wave from the radar system 100 or 200, the distinction between a plurality of measurements is performed by reflected waves obtained by one time of reflection of a radio wave on the reflecting plate 140 or 240, but the present disclosure is not limited to such example. In a case where a plurality of measurement targets fails to be distinguished by a direct wave, the radio wave from the radar system 100 or 200 may be reflected twice or more and then reaches the measurement targets.

FIGS. 12 and 13 are diagrams illustrated to describe an example in which the radio wave from the radar systems 100 or 200 is reflected and then reaches the measurement target. FIG. 12 illustrates an example in which a distance difference is given by reflection twice, and FIG. 13 illustrates an example in which an angle difference is given by reflection twice. In a case where the distance difference or the angle difference fails to be sufficiently (more than the resolution) given by reflection once due to restriction of the installation place or the like, the distance difference or the angle difference may be given by a plurality of times of reflection as illustrated in FIG. 12 or 13.

2. Concluding Remarks

According to the embodiments of the present disclosure as described above, there is provided the radar system 100 capable of distinguishing a plurality of measurement targets and detecting their states independently of installation places even when it is configured with simple configuration having only one of the angular resolution and the distance resolution.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A signal processing device including:

a reception processing unit configured to receive a response to a predetermined signal transmitted from a transmission antenna; and a determination unit configured to determine the plurality of measurement targets by a response to a plurality of signals corresponding to a second direction having a predetermined range different from a first direction having a predetermined range.

(2)

The signal processing device according to (1), in which the determination unit, in a case where a plurality of measurement targets fails to be determined by the response to a plurality of signals corresponding to the first direction, determines the plurality of measurement targets by a response to a plurality of signals corresponding to the second direction.

(3)

The signal processing device according to (1) or (2), in which the transmission antenna has no angular resolution but has distance resolution.

(4)

The signal processing device according to (3), in which the determination unit, in a case where a plurality of measurement targets fails to be determined by the response of a time group earlier in a time direction, determines the plurality of measurement targets by the response of a time group later in the time direction.

(5)

The signal processing device according to (1) or (2), in which the transmission antenna has no distance resolution but has angular resolution.

(6)

The signal processing device according to (5), in which the determination unit, in a case where a plurality of measurement targets fails to be determined by the response of a first angular group, determines the plurality of measurement targets by the response of a second angular group different from the first angular group.

(7)

The signal processing device according to (1) or (2), in which the first direction is a direction allowing the predetermined signal from the transmission antenna to directly reach toward the measurement targets and the second direction is a direction allowing the predetermined signal from the transmission antenna to be reflected at least once to reach the measurement targets.

(8)

A radar system including:

a transmission antenna configured to output a predetermined signal;

a reception antenna configured to receive a response to the predetermined signal transmitted from the transmission antenna; and a determination unit configured to determine the plurality of measurement targets by a response to a plurality of signals corresponding to a second direction having a predetermined range different from a first direction having a predetermined range.

(9)

The radar system according to (8), in which the determination unit, in a case where a plurality of measurement targets fails to be determined by the response to a plurality of signals corresponding to the first direction, determines the plurality of measurement targets by a response to a plurality of signals corresponding to the second direction.

(10)

The radar system according to (8) or (9), in which the transmission antenna has no angular resolution but has distance resolution.

(11)

The radar system according to (10), in which the determination unit, in a case where a plurality of measurement targets fails to be determined by the response of a time group earlier in a time direction, determines the plurality of measurement targets by the response of a time group later in the time direction.

(12)

The radar system according to (8) or (9), in which the transmission antenna has no distance resolution but has angular resolution.

(13)

The radar system according to (12), in which the determination unit, in a case where a plurality of measurement targets fails to be determined by the response of a first angular group, determines the plurality of measurement targets by the response of a second angular group different from the first angular group.

(14)
The radar system according to (8) or (9),
in which the first direction is a direction allowing the predetermined signal from the transmission antenna to directly reach toward the measurement targets and the second direction is a direction allowing the predetermined signal from the transmission antenna to be reflected at least once to reach the measurement targets.

(15)
A signal processing method including:
receiving a response to a predetermined signal transmitted from a transmission antenna; and
determining the plurality of measurement targets by a response to a plurality of signals corresponding to a second direction having a predetermined range different from a first direction having a predetermined range.

REFERENCE SIGNS LIST 100 radar system
110 transmission antenna
120 reception antenna
130 signal processing device
131 oscillator
132 transmission unit
134 reception unit
135 AD converter
136 processing unit
140 reflecting plate
200 radar system
240 reflecting plate

The invention claimed is:

1. A signal processing device, comprising:
a reception processing unit configured to receive a first response to a specific signal transmitted from a transmission antenna, wherein the first response to the specific signal includes a plurality of signals; and
a determination unit configured to determine a plurality of measurement targets, based on a difference between distances of the plurality of measurement targets obtained by a second response to the plurality of signals corresponding to a first direction having a first range, wherein
the first direction having the first range is different from a second direction having a second range,
the first direction is a direction in which the plurality of signals is reflected at least once to reach the plurality of measurement targets, and
the second direction is a direction in which the plurality of signals is transmitted directly to reach the plurality of measurement targets.

2. The signal processing device according to claim 1, wherein the determination unit is further configured to determine, based on a failure in determination of the plurality of measurement targets by a third response to the plurality of signals corresponding to the second direction, the plurality of measurement targets by the second response to the plurality of signals corresponding to the first direction.

3. The signal processing device according to claim 1, wherein the transmission antenna has no angular resolution but has distance resolution.

4. The signal processing device according to claim 3, wherein the determination unit is further configured to determine, based on a failure in determination of the plurality of measurement targets by a fourth response of a first time group earlier in a time direction, the plurality of measurement targets by a fifth response of a second time group later in the time direction.

5. The signal processing device according to claim 1, wherein the transmission antenna has no distance resolution but has angular resolution.

6. The signal processing device according to claim 5, wherein the determination unit is further configured to determine, based on a failure in determination of the plurality of measurement targets by a fourth response of a first angular group, the plurality of measurement targets by a fifth response of a second angular group different from the first angular group.

7. A radar system, comprising:
a transmission antenna configured to output a specific signal;
a reception antenna configured to receive a first response to the specific signal transmitted from the transmission antenna, wherein the first response to the specific signal includes a plurality of signals; and
a determination unit configured to determine a plurality of measurement targets, based on a difference between distances of the plurality of measurement targets obtained by a second response to the plurality of signals corresponding to a first direction having a first range, wherein
the first direction having the first range is different from a second direction having a second range,
the first direction is a direction in which the plurality of signals is reflected at least once to reach the plurality of measurement targets, and
the second direction is a direction in which the plurality of signals is transmitted directly to reach the plurality of measurement targets.

8. The radar system according to claim 7, wherein the determination unit is further configured to determine, based on a failure in determination of the plurality of measurement targets by a third response to the plurality of signals corresponding to the second direction, the plurality of measurement targets by the second response to the plurality of signals corresponding to the first direction.

9. The radar system according to claim 7, wherein the transmission antenna has no angular resolution but has distance resolution.

10. The radar system according to claim 9, wherein the determination unit is further configured to determine, based on a failure in determination of the plurality of measurement targets by a fourth response of a first time group earlier in a time direction, the plurality of measurement targets by a fifth response of a second time group later in the time direction.

11. The radar system according to claim 7, wherein the transmission antenna has no distance resolution but has angular resolution.

12. The radar system according to claim 11, wherein the determination unit is further configured to determine, based on a failure in determination of the plurality of measurement targets by a fourth response of a first angular group, the plurality of measurement targets by a fifth response of a second angular group different from the first angular group.

13. A signal processing method, comprising:
receiving a first response to a specific signal transmitted from a transmission antenna, wherein the first response to the specific signal includes a plurality of signals; and
determining a plurality of measurement targets, based on a difference between distances of the plurality of measurement targets obtained by a second response to the plurality of signals corresponding to a first direction having a first range, wherein
the first direction having the first range is different from a second direction having a second range,
the first direction is a direction in which the plurality of signals is reflected at least once to reach the plurality of measurement targets, and
the second direction is a direction in which the plurality of signals is transmitted directly to reach the plurality of measurement targets.

* * * * *